United States Patent [19]

Hain et al.

[11] Patent Number: 5,294,389

[45] Date of Patent: Mar. 15, 1994

[54] DYNAMIC TREATMENT OF SUTURE STRAND

[75] Inventors: Matthew E. Hain, New Haven; Michael P. Chesterfield, Norwalk; Ilya Koyfman, Orange, all of Conn.

[73] Assignee: United States Surgical Corporation, Norwalk, Conn.

[21] Appl. No.: 52,799

[22] Filed: Apr. 26, 1993

Related U.S. Application Data

[63] Continuation of Ser. No. 715,333, Jun. 14, 1991, abandoned.

[51] Int. Cl.⁵ .................... D01D 10/02; D01D 10/04; D01D 10/06
[52] U.S. Cl. .................... 264/85; 264/103; 264/233; 264/289.6; 264/290.5; 264/342 RE; 264/344; 264/345
[58] Field of Search ............. 264/85, 103, 233, 289.6, 264/290.5, 342 RE, 344, 345

[56] References Cited

U.S. PATENT DOCUMENTS

| | | | |
|---|---|---|---|
| 2,221,351 | 11/1940 | Kempf | 34/187 |
| 2,325,060 | 7/1943 | Ingersoll | 264/232 |
| 2,509,741 | 5/1950 | Miles | 264/103 |
| 3,133,138 | 5/1964 | Alexander, Jr. | 264/290.5 |
| 3,159,964 | 12/1964 | Kretsch | 264/289.6 |
| 3,161,913 | 12/1964 | Pound | 264/289.6 |
| 3,225,534 | 12/1965 | Knospe | 57/140 |
| 3,361,728 | 1/1968 | Coen et al. | 264/216 |
| 3,387,833 | 6/1968 | Whittaker et al. | 261/3 |
| 3,413,397 | 11/1968 | Bierbaum | 264/290.5 |
| 3,422,181 | 1/1969 | Chirgwin | 264/345 |
| 3,432,590 | 3/1969 | Papps | 264/342 |
| 3,460,215 | 8/1969 | Graf | 264/342 |
| 3,471,608 | 10/1969 | Schippers | 264/85 |
| 3,493,646 | 2/1970 | Larkin et al. | 264/346 |
| 3,560,604 | 2/1971 | Papps | 264/168 |
| 3,626,948 | 12/1971 | Glick et al. | 128/335.5 |
| 3,630,205 | 12/1971 | Listner | 128/335.5 |
| 3,739,056 | 6/1973 | Evans et al. | 264/346 |
| 3,772,420 | 11/1973 | Glick et al. | 264/345 |
| 3,833,708 | 9/1974 | Miller et al. | 264/344 |
| 3,905,076 | 9/1975 | Harris | 264/290.5 |
| 3,978,192 | 8/1976 | Sussman | 264/290.5 |
| 4,055,696 | 10/1977 | Kamada et al. | 264/210.8 |
| 4,160,799 | 7/1979 | Locey et al. | 264/342 RE |
| 4,304,648 | 12/1981 | Smith et al. | 34/92 |
| 4,311,660 | 1/1982 | Barham et al. | 264/346 |
| 4,455,273 | 6/1984 | Harpell et al. | 264/257 |
| 4,545,135 | 10/1985 | Barriquand et al. | 34/187 |
| 4,769,922 | 9/1988 | Jansson et al. | 34/92 |
| 4,891,872 | 1/1990 | Sussman | 264/290.5 |
| 4,902,462 | 2/1990 | Bert | 264/210.8 |
| 4,911,165 | 3/1990 | Lennard et al. | 264/235.6 |
| 4,940,559 | 7/1990 | Kretschmann et al. | 264/130 |
| 5,007,922 | 4/1991 | Chen et al. | 606/228 |
| 5,051,272 | 9/1991 | Hermes et al. | 427/2 |
| 5,066,439 | 11/1991 | Nishikawa et al. | 264/103 |
| 5,079,854 | 1/1992 | Hammond et al. | 34/187 |

FOREIGN PATENT DOCUMENTS

| | | | |
|---|---|---|---|
| 2436665 | 2/1975 | Fed. Rep. of Germany . | |
| 60-21213 | 2/1985 | Japan | 264/345 |

OTHER PUBLICATIONS

Shah, R. A. "Incremental Draw Processing of Polyethylene Terephthalate". M. S. Thesis, Tufts University (Oct. 1976).

Primary Examiner—Leo B. Tentoni

[57] ABSTRACT

A suture strand is subjected to dynamic treatment by passing the suture with multiple turns around at least two godets located within a heating zone provided by an oven. The suture strand can be bioabsorbable or non-bioabsorbable, and either monofilament or multifilament. A combination of large and small diameter godets in the oven can achieve dynamic relaxation or stretching.

20 Claims, 6 Drawing Sheets

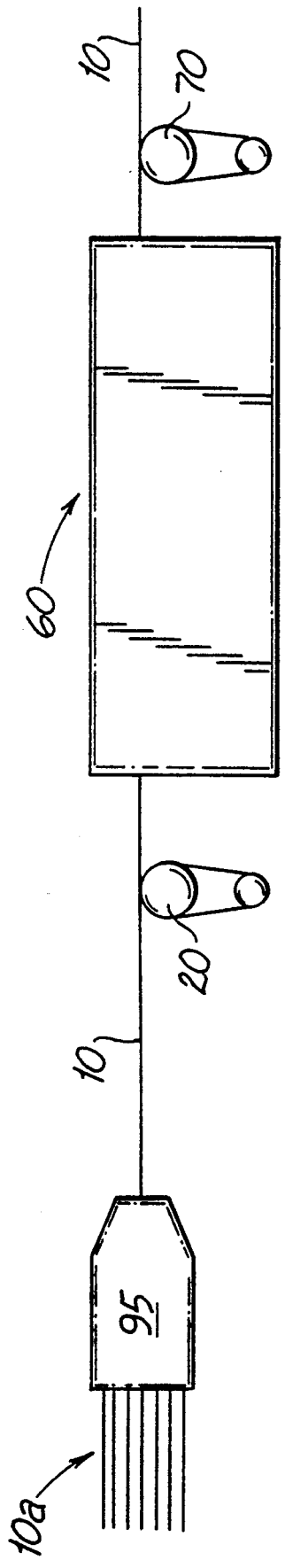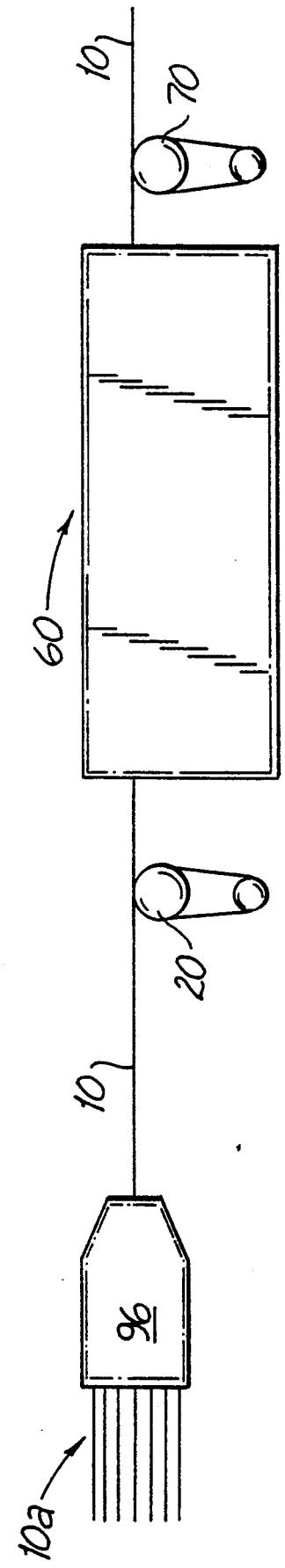

DYNAMIC TREATMENT OF SUTURE STRAND

This is a continuation of Ser. No. 07/715,333 filed Jun. 14, 1991, now abandoned.

BACKGROUND OF THE INVENTION

1. Field of the Invention

This invention relates to a method and apparatus for treating monofilament or multifilament material and more particularly to a method and apparatus for continuously treating a surgical suture strand.

2. Background of the Art

Surgical suture strands or threads often require post-treatment. Bioabsorbable sutures fabricated from homopolymers or copolymers of glycolide, lactide, and other bioabsorbable polymers are currently in widespread use in surgical procedures. Such sutures are often spun from multiple filaments to form a braided suture. One problem is that the finished suture often contains residual amounts of monomer, and other contaminants, which leads to a shortened in-vivo suture strength, i.e., the suture absorption rate is too rapid. Monomer residue can result from incomplete polymerization. Also, the spinning process can form monomer.

One way of removing the monomer and other vaporizable contaminants, is to heat the suture material in a vacuum and/or under the flow of a dry nitrogen atmosphere. Presently, suture post-treatment is accomplished by a static batch process in which the finished suture is wound around a spool, and the spool is placed in a heating chamber under the appropriate atmosphere. One such method is exemplified in U.S. Pat. No. 3,772,420 to Glick, which discloses a method for improving the in-vivo strength of polyglycolic acid braid by wrapping the braid around a cylinder and placing the braid and cylinder in a vacuum chamber held at from 100° to about 150° for a period of time of from about 1 to 3 hours. This method possess the disadvantage of uneven removal of monomer. The monomer from the threads near the exterior of the spool is easily removed whereas the monomer from inside the spool of suture thread must travel through many more layers of suture to be removed.

In addition to modification of the suture composition, suture post-treatment can often be required for mechanical modification such as stretching or relaxing a thread. Sutures of monofilament polypropylene, for example, are relaxed to decrease stiffness, and to increase elongation at breaking point. Up to now, batch processes have been used for polypropylene filament relaxation.

SUMMARY OF THE INVENTION

A method and apparatus is provided herein for the treatment of surgical suture strand. The terms "strand" and "thread" are used interchangeably herein. The method includes continuously passing the strand with plural turns around at least two spaced apart rotatable bodies located within an at least partially enclosed heating zone to effect treatment of said strand. Bioabsorbable or nonbioabsorbable sutures can be thus treated. Likewise, the suture may be multifilament or monofilament. Heating is carried out in an oven under conditions of temperature and residence time so as to increase the in-vivo strength retention of the bioabsorbable filament material by driving off volatile contaminants from the suture. The rotatable bodies, or godets, are positioned such that their respective axes of rotation are parallel to each other and transverse to the lengthwise orientation of the suture.

BRIEF DESCRIPTION OF THE DRAWINGS

FIGS. 5a and 5b diagrammatically illustrate the apparatus of the present invention used in conjunction with, respectively, a braiding means, and a twisting means.

DETAILED DESCRIPTION OF PREFERRED EMBODIMENTS

In accordance with the method of the present invention a suture strand is fed into an oven or other heating means using an input godet, at least two oven godets, and an exit godet, and then either wound onto a spool or subjected to further treatment such as washing, etc. The suture may be fabricated from bioabsorbable materials such as homopolymers or copolymers of glycolide, lactide, caprolactone, or other bioabsorbable polymers. Alternatively, the suture strand may be fabricated from non-bioabsorbable material, such as polypropylene. The suture may be a monofilament, or multifilament strand (e.g., braided suture). The godets can rotate so as to send the suture through the oven at a constant speed. Alternatively, dynamic stretching or dynamic relaxation of the suture may be achieved by using godets of different diameters or by adjusting the speed of the oven godets with respect to the entrance or exit godets.

Figure 1A:
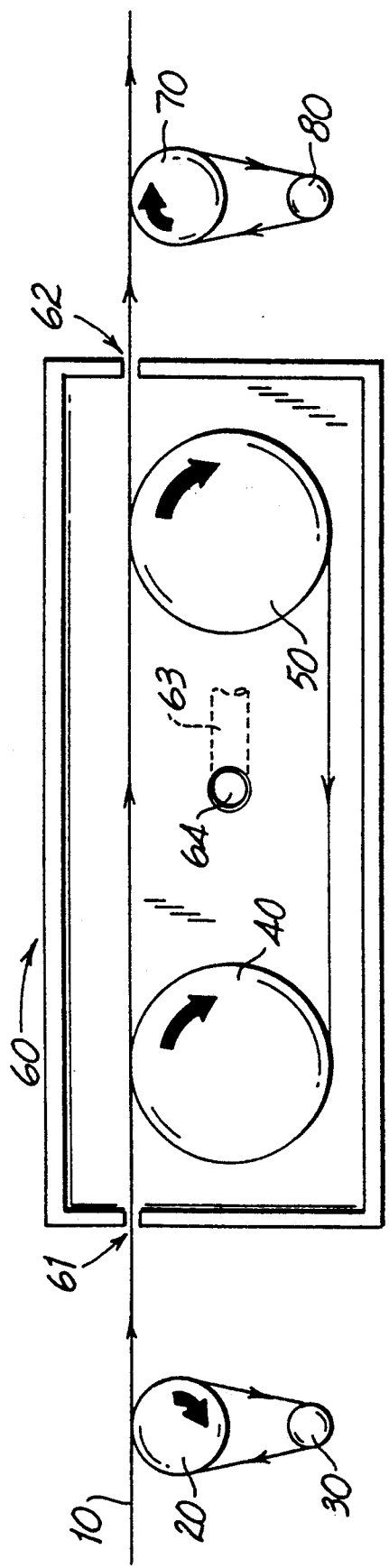
FIGS. 1a and 1b show partially cut away front elevational and top plan views, respectively, of an embodiment of the present invention.
Figure 1B:
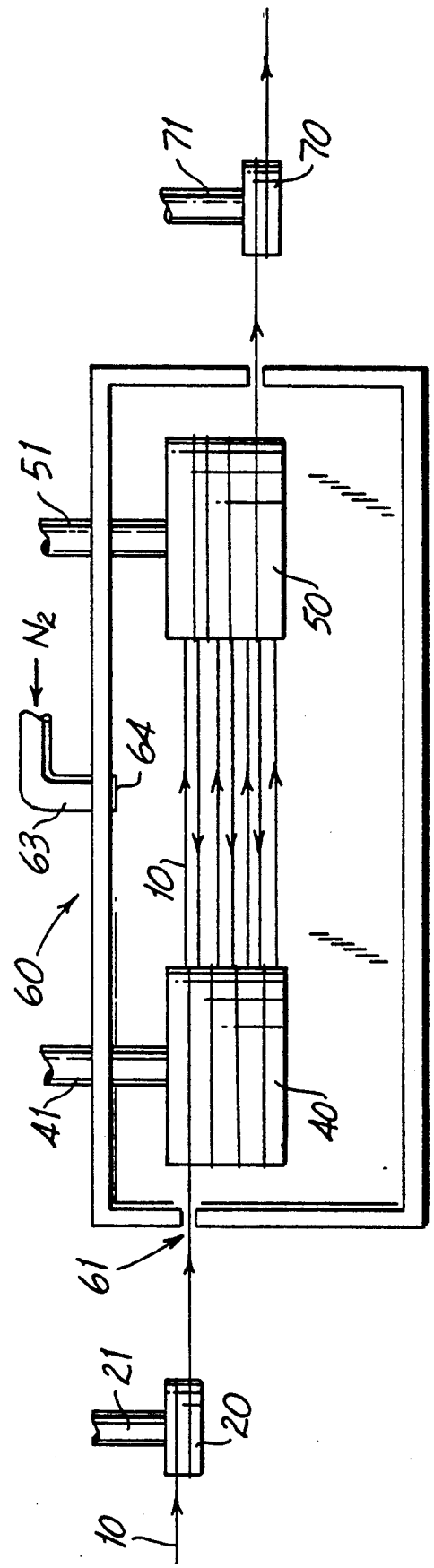

Referring to FIGS. 1a and 1b, an embodiment of the apparatus of the present invention is illustrated wherein suture 10 is passed around input godets 20 and 30, each godet being rotatably mounted by means of its respective axle. Suture 10 thereafter enters oven 60 via entrance aperture 61 and is passed with multiple turns around oven godets 40 and 50. The suture strand then exits the oven via aperture 62 and passes around exit godets 70 and 80. The godets are mounted such that their respective axes of rotation are parallel to each other and transverse to the lengthwise orientation of the suture strand 10. Godets 20, 40, 50, and 70 are mounted to rotatable axles 21, 41, 41 and 71, respectively. Oven godets 40 and 50 rotate at equal speeds so as to move the suture continuously through the oven at a linear speed of about three to six meters per minute. This speed range gives the suture a residence time in the oven of about 22 to 11 minutes. The oven temperature is held at about 120 to 150 degrees centigrade. Generally, lower temperatures require longer residence times and higher temperatures require shorter residence times. Dry nitrogen, or any other relatively inert gas, is pumped in through gas line 63 and enters the oven at aperture 64. The oven temperature and the residence time may be adjusted to achieve the desired level of treatment. Residual monomer dimer, water and/or other volatile contaminants are driven out of the suture.

Since all sides of the suture are exposed to the heated dry atmosphere the treatment is not limited by the time it takes for monomer to be removed from the bottom suture layer of a wound spool (i.e., as with the previously described prior art method of batch treatment of a prewound spool), and may be completed in less time.

A further advantage of the method of the present invention is that the suture is under uniformly applied tension throughout its passage through the oven. Such is not the case with the batch treatment of a prewound spool. The suture threads near the outside of a wound spool are under lesser tension than the threads at the core of the spool because the outside threads have a greater cushioning effect on the surrounding threads whereas the threads at the core are more tightly held. Thus, with the prior known batch process, under the influence of the oven heat the suture may expand or contract unevenly, thereby resulting in a non-uniform diameter. This difficulty is avoided by the method and apparatus of the present invention. Even in the embodiments of the invention described below wherein it is desired to relax or stretch the suture during its passage through the oven, the resulting contraction or expansion occurs uniformly along the entire running length of the suture.

Figure 2A:
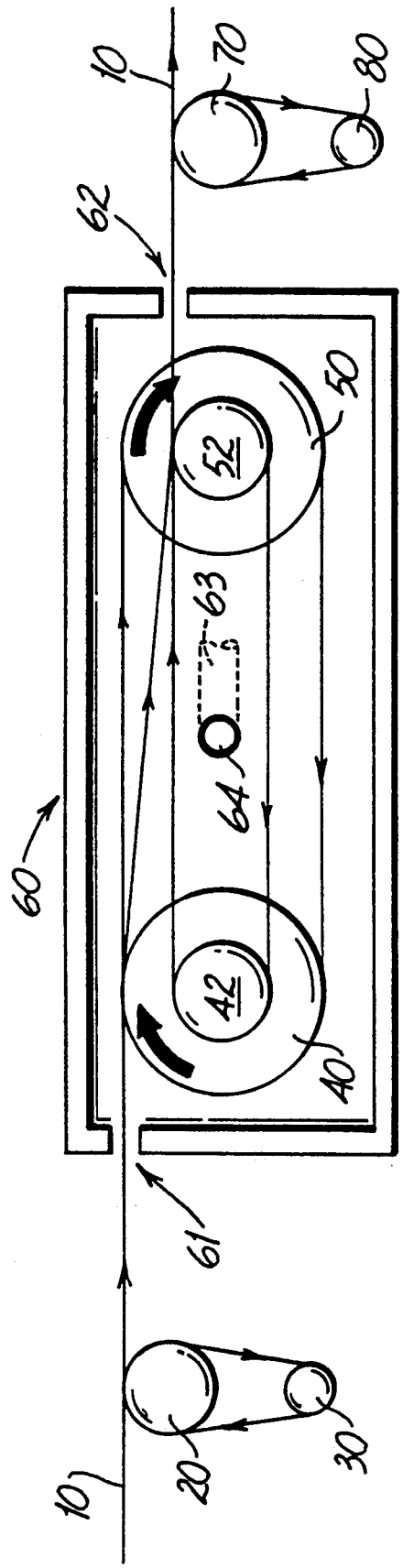
FIGS. 2a and 2b show partially cut away front elevational and top plan views, respectively, of an alternative embodiment of the apparatus of the present invention.
Figure 2B:
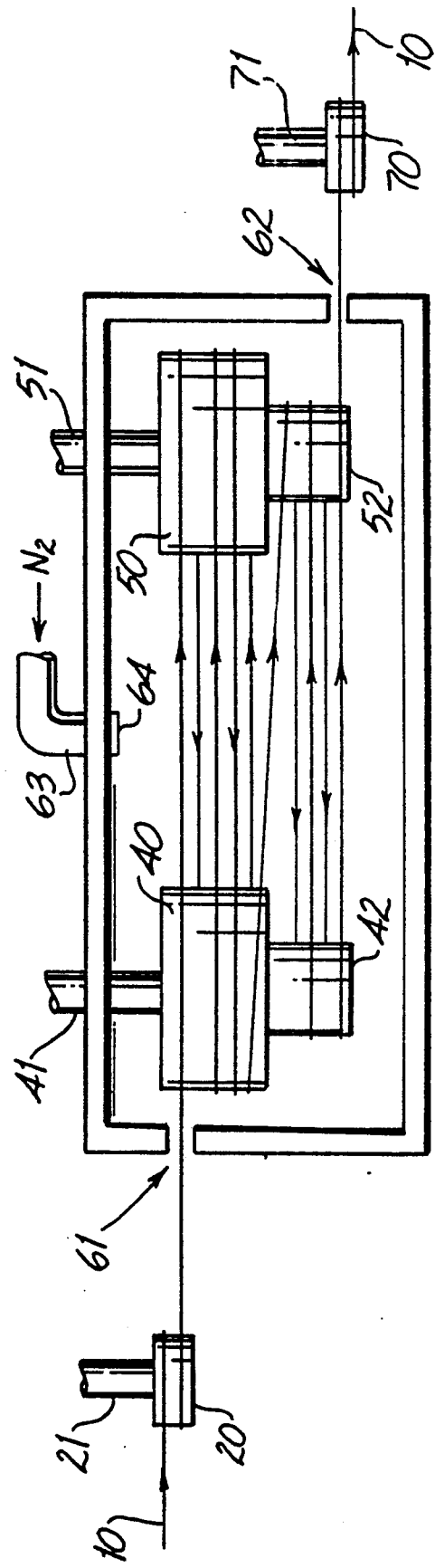

Referring to FIGS. 2a and 2b, a second embodiment of the apparatus of the present invention is illustrated. as with the embodiment described above, suture 10 is passed around input godets 20 and 30 each godet being rotatably mounted by means of its respective axle. Suture 10 thereafter enters oven 60 via entrance aperture 61 and is passed around oven godets 40 and 50. Unlike the apparatus of the first embodiment, relaxation godets of lesser diameter than godets 40 and 50 are included and after multiple turns around godets 40 and 50 the suture strand 10 is then passed with multiple turns around godets 42 and 52 from which the suture strand is finally drawn off. Aperture 62 and godets 70 and 80 are located so as to accommodate the egress of the suture strand 10. Relaxation godets 42 and 52 are fixed to godets 40 and 50 respectively and may be of integral construction therewith. Or, in other words, relaxation godets 42 and 52 may be considered as smaller diameter portions of the respective larger godets. Lesser diameter godets 42 and 52 are coaxially positioned relative to their respective larger godets 40 and 50, and all oven godets 40, 42, 50, and 52 have the same rotational speed. Since the circumferences of lesser diameter godets 42 and 52 are less than the circumference of the respective godets 40 and 50, the tangential surface velocity of godets 42 and 52 is less than that of godets 40 and 50. A suture drawn off a larger oven godet onto a smaller diameter godet undergoes a decrease in linear velocity. The decrease in suture linear velocity accommodates suture relaxation wherein a suture, such as a polypropylene monofilament suture, undergoes an expansion of diameter and a corresponding shrinkage of length under the influence of heat.

Figure 3A:
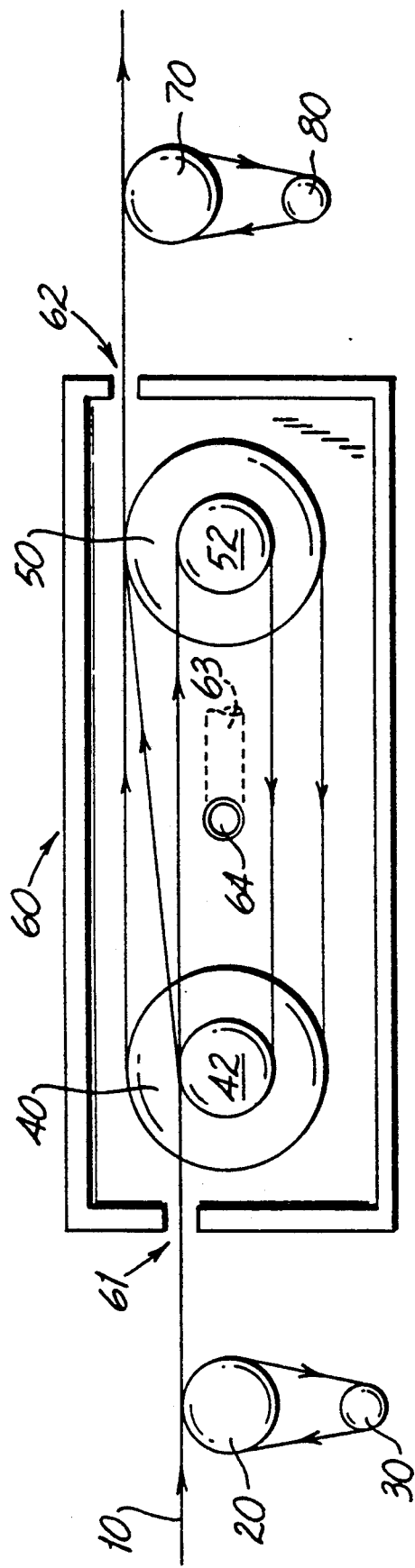
FIGS. 3a and 3b show partially cut away front elevational and top plan views, respectively, of an alternative embodiment of the method and apparatus of the present invention.
Figure 3B:
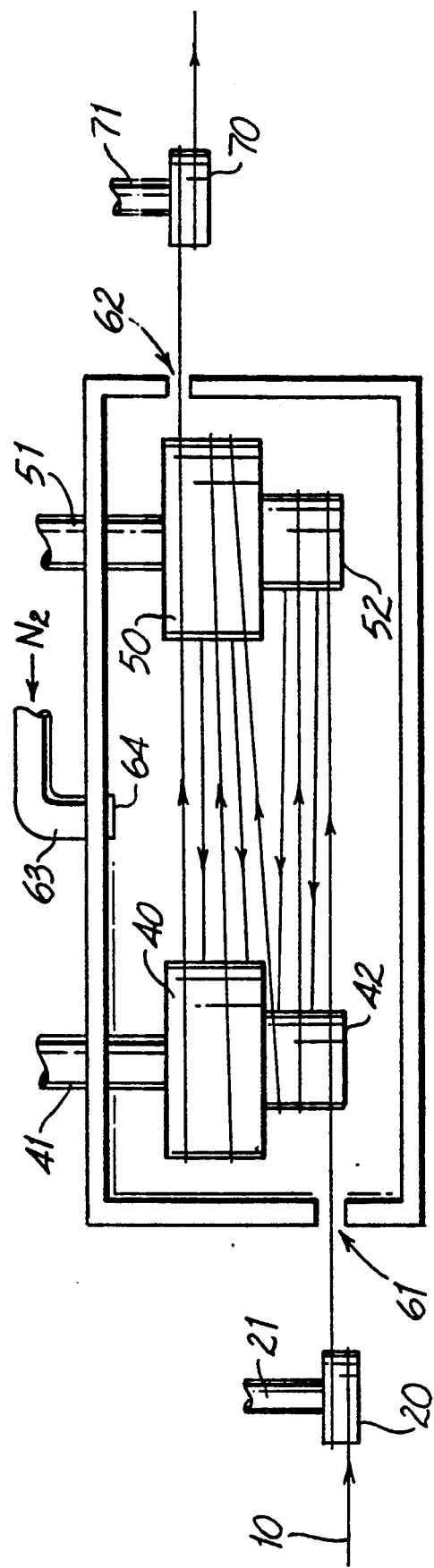

The apparatus as shown in FIGS. 2a and 2b can also be used for the stretching of suture filament strands. Referring to the apparatus illustrated in FIGS. 3a and 3b, the apparatus is similar to that shown in FIGS. 2a and 2b except that aperture 61 and godets 20 and 30 are positioned so as to accommodate entry of the suture strand 10 and initial winding onto the smaller godets 41 and 52. After multiple turns around the smaller godets 42 and 52, suture strand 10 is then passed onto larger diameter godets 40 and 50. The suture 10 undergoes stretching because the tangential surface velocity of godets 40 and 50 is greater than that of smaller godets 42 and 52, as explained above. Thus, suture 10 exits with a smaller diameter than at entry.

As discussed above with respect to the apparatus and methods illustrated in FIGS. 2a, 2b, 3a, and 3b, stretching and relaxation can be performed while in the oven under the conditions of heat, atmosphere, and residence time as previously mentioned. It should be noted that the apparatus as shown in FIG. 1, can also perform the functions of stretching or relaxation. For example, referring again to FIG. 1, the rotational speed of oven godets 40 and 50 may be adjusted such that the tangential surface velocity exceeds that of the input godet 20. Under such a condition, the suture strand will be stretched as it enters the oven and before it has been heated. Alternatively, the exit godet 70 can be rotated with higher surface speed with respect to oven godets 40 and 50 so as to achieve stretching as the suture is drawn out of the oven after being heated.

Figure 4:
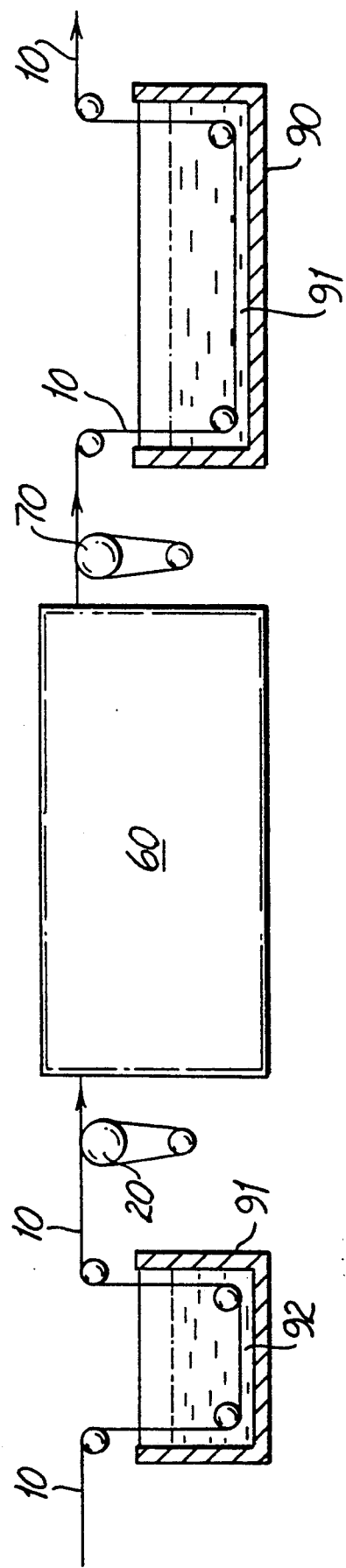
FIG. 4 illustrates suture washing in conjunction with the dynamic treatment method and apparatus of the present invention.

Other modifications of the present invention are contemplated. For example, referring to FIG. 4, before passing around the input godet 20 the suture strand 10 can be subjected to prewash in tank 92 in washing fluid 91. Likewise, after exiting oven 60, suture 10 can be drawn off the output godet 70 and washed in tank 90 containing a washing fluid 91. Contemplated washing fluids include water or chlorofluorocarbons (e.g. FREON TM compounds), the effectiveness of which may be increased through use of an ultrasonic apparatus. After being washed and dried, the suture may be wound for storage on a take-up spool.

Advantageously, other processes may be incorporated into a continuous suture preparation process. Diagrammatically illustrated in FIG. 5a, for example, the suture 10 can be fabricated from multiple individual filaments by means of braider 95, drawn off continuously from the braider, washed, and subjected to the dynamic treatment method of the present invention. Alternatives to braiding such as up twisting, front twisting, back twisting, and other suture fabrication techniques are also well known in the art and, as shown in FIG. 5b which diagrammatically illustrates a twisting means 96, may be incorporated into a continuous process with the dynamic treatment method of the present invention.

Figure 6:
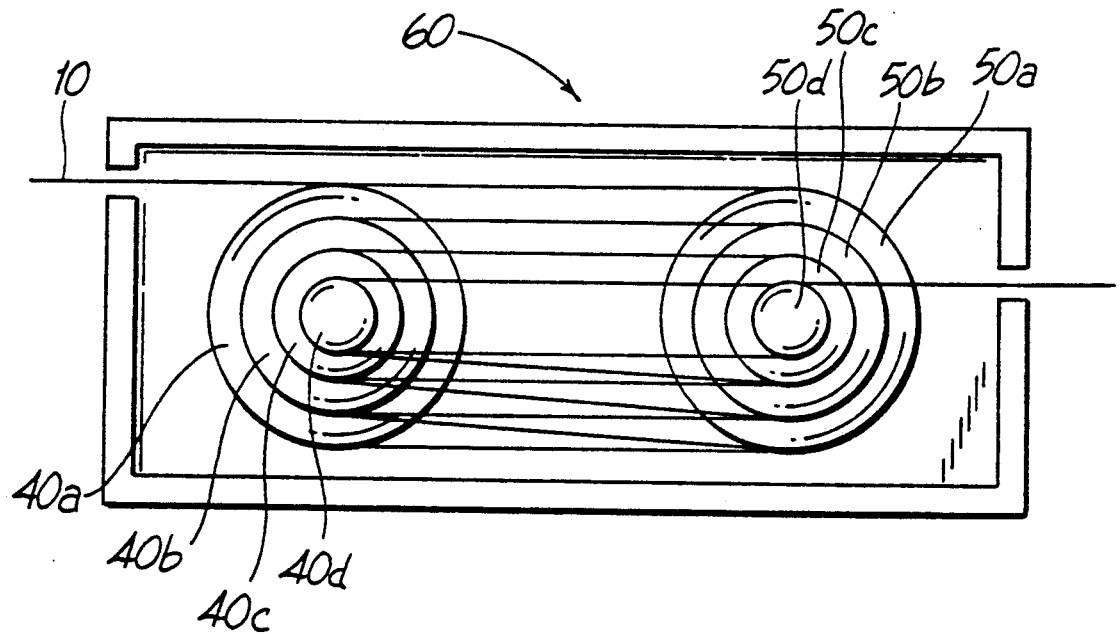
FIG. 6 illustrates an alternative embodiment of the present invention employing stepped godets.
Figure 7:
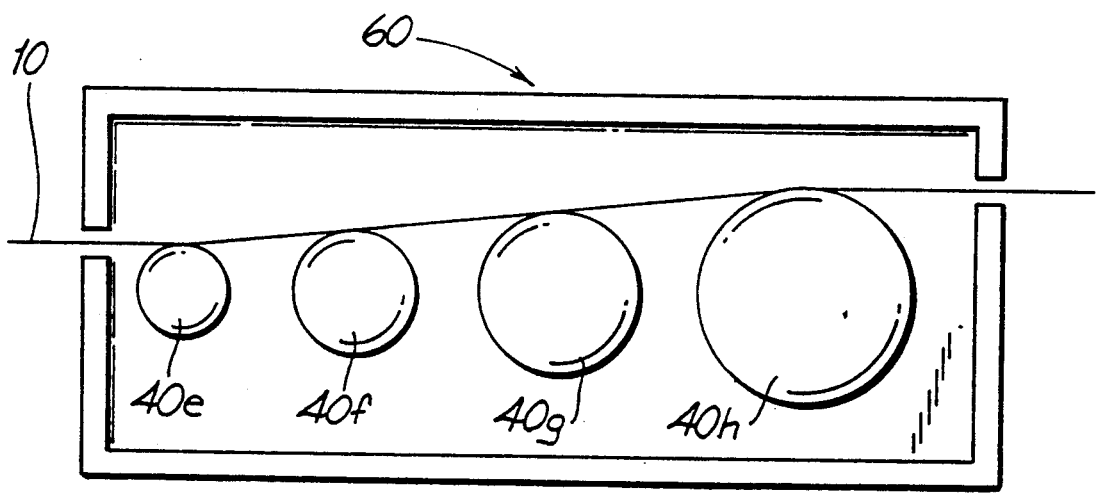
FIG. 7 illustrates an alternative embodiment of the present invention employing different sized godets.

FIGS. 6 and 7 show yet further alternatives to the suture dynamic treatment method. For example, as shown in FIG. 5, suture 10 may be wound around stepped godets having different diameter portions 40a, 40b, 40c, 40d and 50a, 50b, 50c, 50d, respectively. Thus the suture 10 may be stretched or relaxed in gradations within oven 60.

Another way of achieving gradations in suture relaxation or stretching is by using a series of godets 40e, 40f, 40g, and 40h in an oven, as shown in FIG. 6. Godets 40e, 40f, 40g and 40h may be of different diameter and/or they may be the same diameter but rotated at different speeds, and/or they can be spaced apart at varying distances.

What is claimed is:

1. A method for treating surgical suture strand, comprising:
 continuously passing the strand with multiple turns around at least two spaced apart rotatable bodies located within an at least partially enclosed heating zone and in a flowing inert gas atmosphere to effect treatment of said strand.

2. The method of claim 1, wherein said surgical suture strand is fabricated from a bioabsorbable material.

3. The method of claim 2, wherein the heating is carried out under conditions of temperature and residence time so as to increase the in-vivo strength retention of the bioabsorbable material by driving impurities from said strand.

4. The method of claim 3, wherein said conditions of temperature and residence time include a temperature of from about 120° C. to about 150° C. and a residence time of from about 11 minutes to about 22 minutes.

5. The method of claim 2, wherein said bioabsorbable material is selected from the group consisting of polymers of glycolide, lactide, caprolactone, and combinations thereof.

6. The method of claim 1, wherein said inert gas is nitrogen.

7. The method of claim 1, wherein said at least partially enclosed heating zone is provided by an oven.

8. The method of claim 1, wherein said at least two spaced-apart rotatable bodies comprise first and second substantially cylindrically shaped godets each having a circumferential surface for contacting said suture strand, and positioned such that their respective axes of rotation are parallel to each other and substantially transverse to the lengthwise orientation of the suture strand.

9. The method of claim 8, further comprising continuously relaxing said strand in said heating zone to decrease the strand length and increase the strand diameter.

10. The method of claim 9, wherein said first and second godets each have a substantially cylindrical shaped portion of smaller diameter projecting coaxially therefrom, and wherein said relaxing of said strand is accomplished by continuously passing said suture strand with multiple turns around the circumferential surface of said first and second godets, and then passing the suture strand around the circumferential surfaces of said smaller diameter portions.

11. The method of claim 8, further comprising stretching the suture strand in the heating zone.

12. The method of claim 11, wherein said first and second godets each have a substantially cylindrical shaped portion of smaller diameter projecting coaxially therefrom, and said stretching is accomplished by continuously passing said suture strand with multiple turns around said smaller diameter portions, and then passing said suture strand around the circumferential surfaces of the first and second godets with multiple turns.

13. The method of claim 8, further comprising stretching the suture strand outside the heating zone.

14. The method of claim 13, wherein said stretching of the suture strand outside the heating zone is accomplished by maintaining a rotational speed of the first and second godets such that the tangential surface of velocity of the first and second godets is greater than the linear velocity of suture strand at a point prior to entering the heating zone.

15. The method of claim 1, wherein said suture strand is a multifilament strand.

16. The method of claim 15, wherein said multifilament suture is braided.

17. The method of claim 1 wherein said suture strand is a monofilament strand.

18. The method of claim 1, further including immersing said suture strand in a bath of washing fluid.

19. The method of claim 1, further including braiding the suture strand with braiding means, continuously drawing off the suture strand from said braiding means, and thereafter continuously passing the suture strand around said at least one rotatable body.

20. The method of claim 1, further including twisting the suture strand with twisting means, continuously drawing off the suture strand from said twisting means, and thereafter continuously passing the suture strand around said at least one rotatable body.

* * * * *